(12) United States Patent
Chen et al.

(10) Patent No.: US 8,840,775 B2
(45) Date of Patent: Sep. 23, 2014

(54) REGENERATIVE GAS SENSOR

(75) Inventors: Lei Chen, South Windsor, CT (US);
Zhiwei Yang, South Windsor, CT (US);
Antonio M. Vincitore, South Windsor,
CT (US); Joseph J. Sangiovanni, West
Suffield, CT (US)

(73) Assignee: UTC Fire & Security Corporation,
Farmington, CT (US)

( * ) Notice: Subject to any disclaimer, the term of this
patent is extended or adjusted under 35
U.S.C. 154(b) by 192 days.

(21) Appl. No.: 13/328,558

(22) Filed: Dec. 16, 2011

(65) Prior Publication Data

US 2013/0153442 A1 Jun. 20, 2013

(51) Int. Cl.
*G01N 27/30* (2006.01)
*G01N 27/407* (2006.01)

(52) U.S. Cl.
CPC ........................... *G01N 27/30* (2013.01);
*G01N 27/407* (2013.01)
USPC ...... 205/786.5; 73/23.31; 73/23.32; 204/431;
205/785.5

(58) Field of Classification Search
CPC .............................. G01N 27/30; G01N 27/407
USPC ...................... 204/421–429; 73/23.31, 23.32;
205/786.5, 785.5
See application file for complete search history.

(56) References Cited

U.S. PATENT DOCUMENTS

| | | | |
|---|---|---|---|
| 4,636,294 A | 1/1987 | Novack et al. | |
| 5,667,653 A | 9/1997 | Schneider et al. | |
| 5,716,506 A * | 2/1998 | Maclay et al. | 204/424 |
| 7,060,169 B2 | 6/2006 | Rohrl | |
| 7,413,645 B2 * | 8/2008 | Scheffler | 205/775 |
| 2003/0038029 A1 | 2/2003 | Davis et al. | |
| 2003/0217922 A1 * | 11/2003 | Suganuma et al. | 204/426 |
| 2004/0033414 A1 | 2/2004 | Rohrl | |
| 2005/0194264 A1 | 9/2005 | Dalmia | |
| 2006/0049048 A1 * | 3/2006 | Kondo et al. | 204/425 |
| 2006/0070886 A1 * | 4/2006 | Saunders et al. | 205/341 |
| 2006/0096871 A1 * | 5/2006 | Manoukian et al. | 205/782 |
| 2008/0209876 A1 | 9/2008 | Miller | |
| 2009/0293590 A1 * | 12/2009 | Zeng et al. | 73/24.06 |
| 2010/0012494 A1 | 1/2010 | Kiesele et al. | |

FOREIGN PATENT DOCUMENTS

| | | |
|---|---|---|
| WO | WO2005114162 A1 | 12/2005 |
| WO | WO2010017563 A1 | 2/2010 |
| WO | WO2011036565 A2 | 3/2011 |

OTHER PUBLICATIONS

Scovazzo et al. (Journal of Membrane Science 238 (2004) 57-63).*
Mahony et al. (J. Phys. Chem. C 2009, 113, 10997-11002).*
Choi et al., Analytica Chemica, 431, 2001, 261-267.*

(Continued)

*Primary Examiner* — Jennifer Dieterle
(74) *Attorney, Agent, or Firm* — Cantor Colburn LLP

(57) ABSTRACT

A gas sensor includes a housing having disposed therein a membrane electrode assembly comprising a sensing electrode, a counter electrode, and a polymer membrane disposed between the sensing electrode and the counter electrode. The polymer membrane comprises an ionic liquid retained therein. The sensor also includes a catalyst support that can be stable in a range of potentials to allow for detection mode and catalyst regeneration mode to be operative. The sensor further includes a circuitry and algorithm to implement the catalyst regeneration mechanism electrochemically. The sensor further includes a chamber for reference gas to which the counter electrode is exposed, and a chamber for test gas to which a gas to be tested is exposed. The sensor also includes a pathway for test gas to enter the chamber and a measured electrical circuit connecting the sensing electrode and the counter electrode.

22 Claims, 4 Drawing Sheets

(56) References Cited

OTHER PUBLICATIONS

Nádherná, Martina, et al., "A planar, solid-state amperometric sensor for nitrogen dioxide, employing an ionic liquid electrolyte contained in a polymeric matrix", Sensors and Actuators B: Chemical, vol. 161, No. 1, Nov. 26, 2011, pp. 811-817, XP055061028, ISSN: 0925-4005, DOI: 10.1016/j.snb.2011.11.037.

Wang, Yuorong, et al., "Solid polymer electrolyte-based hydrogen sulfide sensor", Sensors and Actuators B: Chemical, vol. 87, No. 1, Nov. 15, 2002, pp. 115-121, XP004391085, ISSN: 0925-4005, DOI: 10.1016/S0925-4005(02) 00227-7.

Yu, Chunbo, et al., "Electrochemical H2S sensor with H2SO4 pretreated Nafion membrane as solid polymer electrolyte", Sensors and Actuators B: Chemical, vol. 86, No. 2-3, Sep. 20, 2002, pp. 259-265, XP004380199, ISSN: 0925-4005, DOI: 10.1016/S0925-4005(02)00200-9.

International Search Report for International Application No. PCT/US2012/067020 mailed May 8, 2013, 6 pages.

Written Opinion for International Application No. PCT/US2012/067020 mailed May 8, 2013, 8 pages.

* cited by examiner

REGENERATIVE GAS SENSOR

BACKGROUND OF THE INVENTION

Electrochemical gas sensors are widely used for sensing a variety of different gases. Although the specific design features of these sensors can vary widely based on the electrochemical reactions of the gas species being sensed, the environments in which the sensors are used, and other factors, the sensors generally share common features, such as having two electrodes (an anode and a cathode) separated by an electrolyte. Some sensors are susceptible to contamination of catalyst(s) on the sensor electrode(s). For example, electrochemical hydrogen sulfide ($H_2S$) sensors can be susceptible sulfur contamination of catalyst on the electrodes. Electrochemical $H_2S$ sensors generally utilize an anode as a sensing electrode (exposed to air being tested for the presence of $H_2S$) and a cathode as a sealed reference electrode that is exposed to clean air, separated by an electrolyte. The reaction that takes place at the sensing electrode (anode) is set forth as $H_2S + 4H_2O \rightarrow SO_4^{2-} + 10H^+ + 8e^-$. The protons liberated by the reaction taking place at the anode are transferred through the electrolyte to the cathode, where they participate in the reaction $2O_2 + 8H^+ + 8e^- \rightarrow 4H_2O$. The electrons liberated at the anode are conducted to the cathode through a monitored circuit that measures current and/or voltage, with the current/voltage in this circuit being proportional to the concentration of $H_2S$ in the gas being tested. As can be readily seen by combining these chemical equations, the net reaction of the electrode assembly results in no net production or consumption of water.

$H_2S$ detection using polymer electrochemical sensors with a long lifetime has not been practically available because sulfur deposition (dissociative adsorption according to reaction $H_2S+Pt \rightarrow Pt—S+H_2$) occurring on the catalyst can deactivate the sensor. Previous results have shown that exposure to a higher potential (>1.2 V) can mitigate the poisoning by oxidizing the sulfur to $SO_2$, or sulfate or sulfite species as shown by reaction $S—Pt+4H_2O \rightarrow SO_4^{2-}+8H^++6e^-+Pt$. It is desirable to have a $H_2S$ sensor that can regenerate the catalyst to extending operating lifetime. Electrochemically regenerating the catalyst can provide simplicity and reliability of implementation for catalyst regeneration. However, such electrochemical regeneration can result in corrosion of conductive carbon supports often used to form the sensor electrodes.

Some sensor designs have utilized liquid electrolytes such as aqueous sulfuric acid. Such electrolytes, however, are subject to leakage of electrolyte from the sensor assembly, which can expose the surrounding environment to corrosive chemicals, as well as result in degraded performance or failure of the sensor due to electrolyte dry-out. Evaporation of water from such aqueous liquid electrolytes can also result in degraded performance or failure of the sensor. Sensors with such liquid electrolytes can often be utilized only in limited operating environments in terms of temperature and humidity, and also have to include complex design features to isolate the liquid electrolyte from the outside environment. Other designs of sensors propose using solid electrolyte like the ionomer Nafion®, manufactured by the E.I. du Pont de Nemours and Company. An electrode assembly with such a solid electrolytes is known as a membrane electrode assembly ("MEA"). Such ionomeric electrolytes require the presence of water vapor in order to provide the desired electrolyte performance for gas sensors, and sensor designs that use such ionomeric solid electrolytes typically must have a water reservoir integrated with the sensor in order to maintain humidity levels in the ionomeric solid electrolyte. The necessity of a water reservoir adds cost, size, and complexity to the overall sensor design, as well as providing a failure mode for the sensor if the reservoir seal is compromised. Also, since a gas sensor cannot be completely sealed since it must be open at least to the gas being tested, the water reservoir is subject to evaporation and thus has a finite life, which can be further shortened if the sensor is operated in dry and warm environments.

In view of the sometimes demanding requirements for gas sensor electrolytes, various alternatives have been used or proposed. However, new alternatives are always well-received that may be more appropriate for or function better in certain environments, offer better cost, or enable beneficial modifications to the overall sensor design.

BRIEF DESCRIPTION OF THE INVENTION

According to an exemplary embodiment, a gas sensor includes a housing having disposed therein a membrane electrode assembly comprising a sensing electrode, a counter electrode, and a polymer membrane disposed between the sensing electrode and the counter electrode. The sensing electrode and the counter electrode each independently comprises a conductive support having a catalyst thereon (as used herein, "conductive support" refers to an electrically conductive support). The polymer membrane comprises an ionic liquid retained therein. The sensor further includes a chamber for reference gas to which the counter electrode is exposed, and a chamber for test gas to which a gas to be tested is exposed. The sensor also includes a pathway for test gas to enter the chamber, a measurement electrical circuit connecting the sensing electrode and the counter electrode, and an electrical circuit and algorithm for regenerating the catalyst when it is partially or completely deactivated by contaminants. In an exemplary embodiment, the polymer of the polymer membrane and electrodes is a proton conducting ionomer.

In another exemplary embodiment, the membrane includes a polymer matrix and a proton-conducting ionic liquid retained in the matrix. In yet another exemplary embodiment, the membrane includes a proton-conducting ionomer matrix, and a proton-conducting ionic liquid retained in the matrix. In still another exemplary embodiment, the membrane includes a proton-conducting ionic liquid molecule or moiety grafted to a polymer repeat unit or matrix. In a further exemplary embodiment, the sensing electrode (or anode), or both the sensing electrode and the counter electrode (or cathode) can be formed from a conductive support having a catalyst disposed thereon. In a still further exemplary embodiment, the conductive support comprises a conductive metal oxide. In yet a further exemplary embodiment, the conductive support comprises conductive carbon. In an additional exemplary embodiment, the sensor does not include a water reservoir.

The sensor can be operated by generating a difference in electrochemical potential between the sensing electrode and the counter electrode that is responsive to the presence and/or concentration of a gas being tested, measuring voltage or current between the sensing electrode and the counter electrode by an electrical circuit while the sensing and counter electrodes are held at a fixed potential (potentiostatic mode), converting the measured voltage or current to a reading indicative of the presence and/or concentration of the gas being tested, and periodically applying an electrical potential difference across the sensing electrode and the counter electrode to regenerate the catalyst when it is partially or completely deactivated by contaminants. In a further exemplary embodiment, the method of operating the sensor includes adjusting the conversion of measured voltage or current to the reading indicative of the presence and/or concentration of the gas being tested, based on the humidity of the environment, which may be determined by measuring the impedance or conductivity of the MEA. In another exemplary embodiment, the area of sensing electrode (anode) is substantially smaller than that of the counter electrode (cathode) under detection mode such that the potential of the counter electrode remains constant whereby the current-voltage relationship is solely attributed to the electrochemical reaction in the working electrode, leading to more accurate determination of gas concentration.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION OF THE INVENTION

Figure 1:
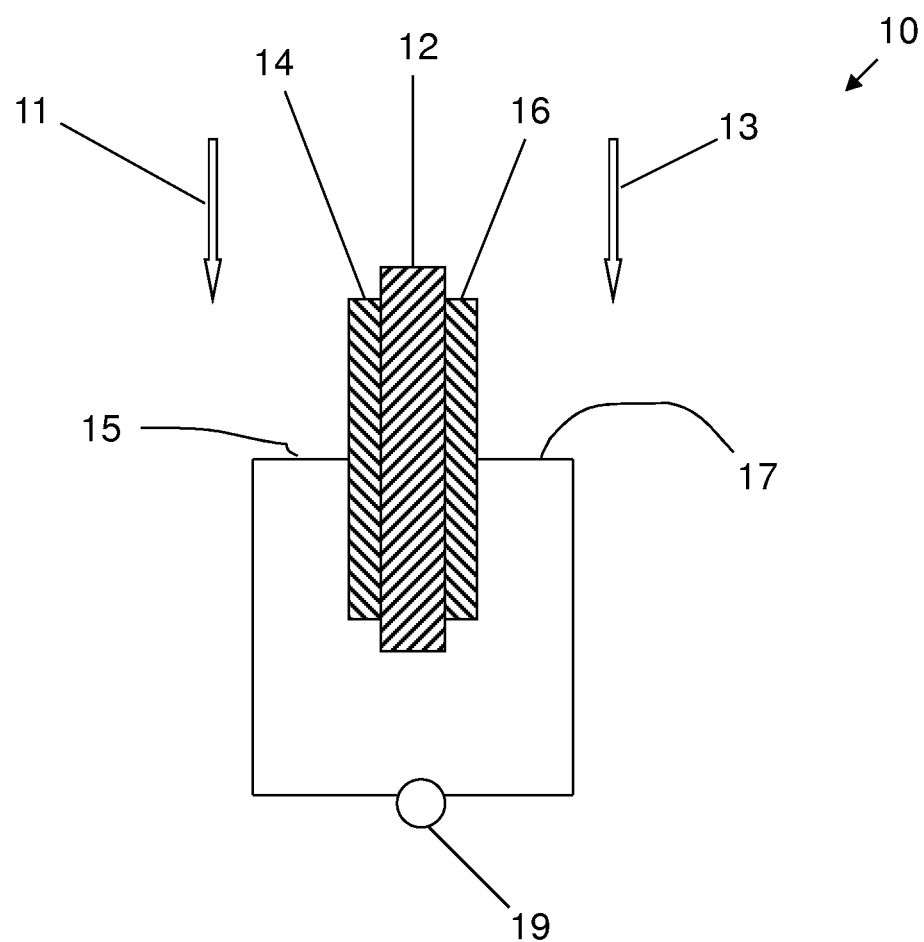
FIG. 1 depicts a simplified schematic representation of a gas sensor as described herein.

A simplified gas sensor is schematically shown in FIG. 1, in which a membrane electrode assembly (MEA) 10 has a polymer membrane 12 with an ionic liquid retained therein disposed between sensing electrode 14 and counter electrode 16. Current collectors 15 and 17 are attached to the electrodes and complete a circuit between the electrodes having a voltmeter or ampere meter 19 disposed therein. The electrodes are exposed to test gas 11 and reference gas 13, which provides an electrical current in the circuit, which can be read by electronic signal processing circuitry 19 for reading the electrical current in the circuit for measuring $H_2S$ concentration and for providing current to regenerate the catalyst. The regeneration circuit can share the same electrical pathway (i.e., wires and electrical connections to the electrodes) as shown in FIG. 1, or they can be independent parallel circuits or they can be connected to the electrodes.

Figure 2:
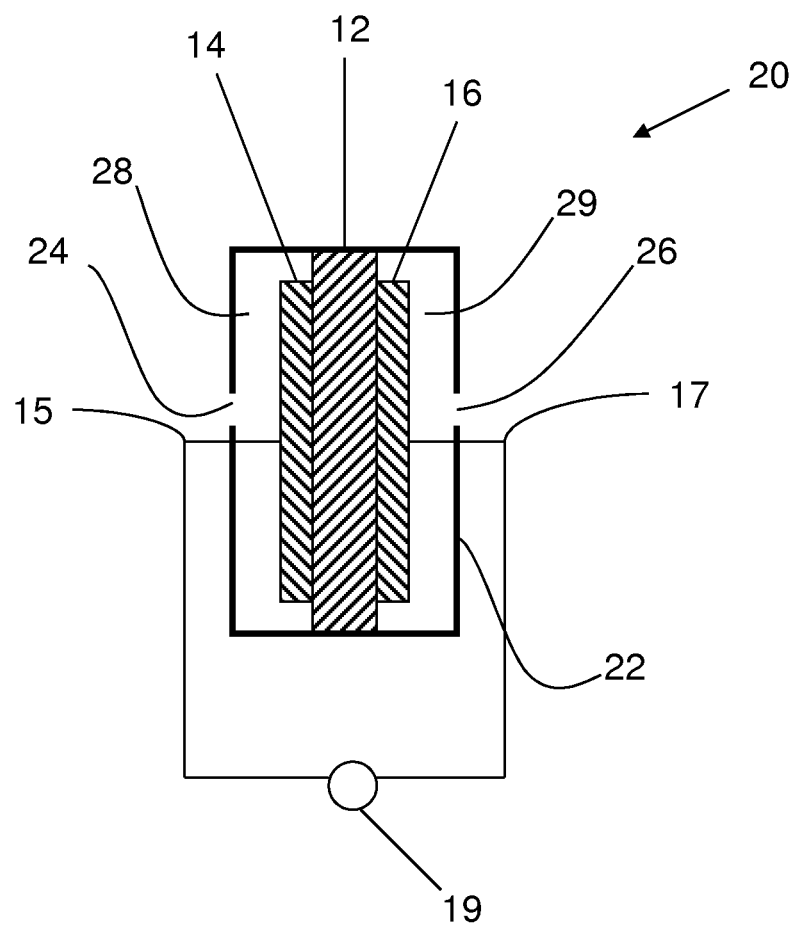
FIG. 2 depicts a simplified schematic representation of a gas sensor as described herein.

The MEA described herein may be incorporated into a gas sensor, which may typically also include a housing, seals, one or more channels or wicking elements to guide test and/or reference gases to the electrodes, electrical connections and wiring (i.e., current collectors). These sensors measure current or voltage generated by the electrochemical reaction(s) utilized in sensing component(s) in the gas being tested, connectors, output displays, and the like. Exemplary gas sensor configurations and variations thereon are disclosed, for example, in U.S. Pat. No. 5,650,054, U.S. Pat. No. 5,573,648, U.S. Pat. No. 6,200,443, U.S. Pat. No. 6,948,352, US 2009/0184005 A1, and US 2010/0012494 A1, the disclosures of which are incorporated herein by reference in their entirety. Unlike some known sensors, the electrode assemblies described herein do not require a water reservoir (and the associated channels or other configuration utilized to deliver water vapor from the reservoir to the MEA), although they may utilize a water reservoir as an optional component. Another simplified schematic drawing of a typical gas sensor is shown in FIG. 2, which depicts a gas sensor 20 having the MEA 10 from FIG. 1 disposed in housing 22 having opening 24 for circulation of a test gas and opening 26 for circulation of a reference gas. The openings are shown as completely open, although it is understood that they may be covered with a screen or gas permeable membrane. Also, the openings are shown for purposes of illustration as leading directly into chambers 28 and 29 for the test gas and the reference gas, respectively, but the gases may also be introduced into interior chambers through channel(s) that lead from an outer surface of the sensor to interior chambers. Also, although FIG. 2 provides an opening 26 for reference gas to enter the reference gas chamber, in certain embodiments the reference gas chamber 29 can be sealed. For example, a hydrogen sulfide sensor only uses up minute amounts of reference oxygen when hydrogen sulfide is present at the sensing electrode, allowing for the reference gas chamber 29 to be sealed. The edges of the electrode assembly membrane 12 are sealed against the inner surface of housing 22 using conventional seals such as rubber rings (not shown) so that the test gas and reference gas are maintained on opposing sides of the MEA, although other techniques known in the art (e.g., disposing the MEA in a frame (not shown) that is sealed to the edges of the housing) can be used. Although the electrodes are shown to be bonded to the electrolyte/membrane in these figures, the entity including two electrodes and a separator membrane also can be mechanically clamped together without compromising the functionalities of the sensor.

Figure 3:
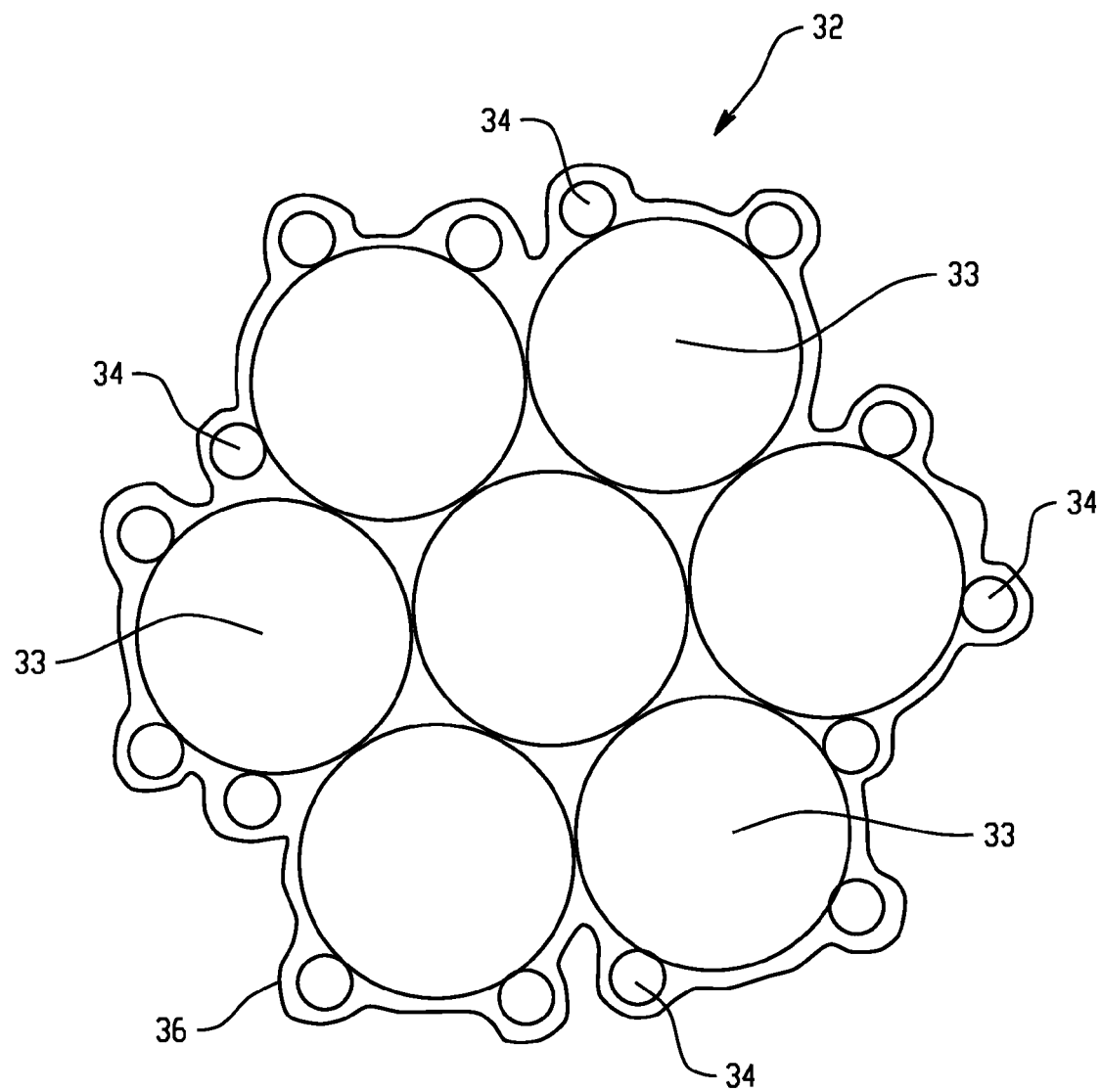
FIG. 3 depicts a schematic representation of an ionomer-covered supported catalyst agglomerate useful for forming the sensing (anode) and counter (cathode) electrodes of a gas sensor as described herein.

The precise composition of the electrodes, and materials used in fabricating them, will depend on the particular electrochemistry involved for the gas being tested. Similarly, the physical configuration of the electrodes will depend on the size and shape of the sensor. For electrochemical reactions that produce low amounts of current, thin electrodes can be utilized to reduce internal ionic resistance, with electrode thicknesses of 1 to 20 μm being useful in an exemplary embodiment of a $H_2S$ sensor. A variety of catalytic metals and alloys (e.g., iridium, rhenium, palladium, platinum, copper, indium, rubidium, silver, gold) supported on a conductive support may be used to form the electrodes. Catalysts can be disposed in both the sensing and the counter electrode to allow tunable sensor performance. Also, the sensing and counter electrodes may each use the same or different types of catalyst(s) and the same or different types of conductive support(s). In an exemplary embodiment, the electrodes may be formed from an agglomerate of a conductive support, a catalyst such as platinum, and a binder such as a proton-conducting ionomer, as shown in FIG. 3. FIG. 3 depicts a portion of an agglomerate 32 having conductive support particles 33 with a nominal diameter of about 30-40 nm, with catalyst particles 34 (nominal diameter of about 1-10 nm) disposed thereon, covered by a thin layer of binder/ionic conductor 36 (e.g., an ionomer such as Nafion®). In an exemplary embodiment, the electrode may also contain an ionic liquid retained (as described below with respect to the polymer membrane) by the ionomer, catalyst-bearing conductive support particles, or both. Electrodes may be deposited (e.g., by screen printing, inkjet printing, metal vapor deposition, casting, or other deposition techniques depending on the composition and characteristics of the electrode) onto a pre-formed electrolyte, or an electrode may be formed first followed by deposition of the electrolyte and then another electrode.

A known side reaction of the main $H_2S$ electrochemical sensing reactions described above is a dissociative adsorption reaction whereby sulfur is adsorbed onto a catalyst such as platinum: $H_2S+Pt \rightarrow Pt-S+H_2$. Over time, the accumulation of sulfur adsorbed onto the catalyst can adversely affect performance of the sensor, even leading to sensor deactivation. Adsorbed sulfur can be removed from the catalyst by applying a potential across the sensing and counter electrodes sufficient to oxidize the sulfur. However, a potential sufficiently high to oxidize adsorbed sulfur (typically >1.2V) can also oxidize conductive carbon that is commonly used as a conductive support. In one exemplary embodiment, the conductive support for the catalyst is a conductive metal oxide. Exemplary conductive metal oxides include but are not limited to $TiO_2$, $WO_3$, $SnO_2$, etc. These conductive metal oxides can be undoped or they can be doped with metals such as Sb, V, Tl, Mn, Co, Fe, etc. In another exemplary embodiment, conductive carbon (e.g., including graphite, grapheme, carbon nanotube, or carbon modified by other elements such as nitrogen) is used as the conductive support and the sensor is free of a water reservoir. Although not being bound by any particular theory, it is believed that the absence of water (which could come from a water reservoir or an aqueous liquid electrolyte, both of which can be avoided by the embodiments described herein) deprives the sensor environment of a source of hydroxyl ions that play a role in oxidation/corrosion of carbon conductive support, as can occur during catalyst regeneration.

In exemplary embodiments as described herein, the electrolyte for an MEA for the sensor is provided by a membrane between the sensing electrode and the reference electrode. This membrane includes an ionic liquid retained therein. Ionic liquids are generally recognized in the scientific literature as being salts having a melting point below 100° C.; however, the melting point for ionic liquids useful in the exemplary embodiments described herein can vary depending on the anticipated operating temperatures of the gas sensor, and could even be higher than 100° C. for high-temperature applications. In exemplary embodiments for sensors to be used in normal ambient conditions, ionic liquids having a melting point below 0° C. will provide performance at temperatures at least as low as the freezing point of water. Many ionic liquids offer high electrochemical stability (e.g., up to roughly 6 V vs. Standard Hydrogen Electrode (SHE), compared to 1.23V vs. SHE for water) and/or high conductivity (>1 mS/cm, and up to 100 mS/cm under ambient temperature). The electrochemical stability and conductivity of ionic liquids used in the electrode assemblies described herein can vary significantly depending on the characteristics and requirements of the electrochemical reactions involved with sensing the gas in question. In one exemplary embodiment, ionic liquids used in these electrode assemblies can have electrochemical stability of from 0 V to 6 V (vs. SHE), more specifically, from 0 to 4.5 V (vs. SHE), and/or a conductivity between 1 mS/cm and 100 mS/cm.

Ionic liquids are well-known, and have been the subject of significant study and research. Ionic liquids tend to be air and water stable. Exemplary cations for ionic liquids used in the embodiments described herein include, but are not limited to imidazolium (e.g., 1-ethyl-3-methylimidazolium, 1-ethyl-2,3-dimethylimidazolium, 1-butyl-3-methylimidazolium ("BMI"), 1-hexyl-3-methyl-imidazolium ("HMI"), pyridinium (e.g., N-methylpyridinium), tetraalkylammonium, pyrrolidinium (e.g. 1-butyl-1-methyl-pyrrolidinium ("BMPyr"), trialkylsulfonium (e.g., triethylsulfonium), pyrazolium, triazolium, thiazolium, oxazolium, pyridazinium, pyrimidinium, pyrazinium. Exemplary anions for ionic liquids used in the embodiments described herein include, but are not limited to, tetrafluoroborate ($BF_4$), hexafluorophosphate ($PF_6$), trifluoromethanesulfonate ($CF_3SO_3$), trifluoroethanoate, nitrate, SCN, $HSO_4$, $HCO_3$, $CH_3SO_3$, $CH_3CH_2SO_4$, $(CH_3(CH_2)_3O)_2POO$, $(CF_3SO_2)_2N$, dicyanamide, $(CF_3CF_2SO_2)_2N$, L-(+)-lactate, $CH_3SO_4$, and $CH_3COO$, and the like.

In one exemplary embodiment, the ionic liquid has a cation that is an imidazolium, and more specifically the ionic liquid has the formula:

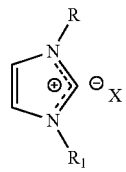

wherein, R and $R_1$ are independently selected from H, an unsubstituted or substituted alkyl group having 1 to 30 carbon atoms, or an unsubstituted or substituted aryl group having 6 to 30 carbon atoms. $X^\ominus$ is an anionic group, as described hereinabove, that associates with imidazolium to form an ionic-liquid cation/anion pair.

As described herein, the ionic liquid is retained in a polymer membrane disposed between two electrodes. The term "retained" is not meant to require absolute retention where it would be impossible for even minute quantities of the ionic liquid to migrate out of the polymer membrane, but rather substantial retention such that ionic liquid is present to impact the ionic characteristics of the polymer membrane. Retention of the ionic liquid in the membrane may be achieved, for example, by including a polymer matrix in the membrane having porosity characteristics such that ionic liquid can be retained within pores, cells, or other interstitial spaces in the polymer matrix. The term matrix includes any configuration of polymer segments and interstitial space between polymer segments that is available for occupation by the molecules and/or atoms of the ionic liquid atoms/molecules, and is not limited to any particular type of regular or irregular configuration. The scale of interspersed polymer segments and ionic liquid can be from angstrom to sub-micrometer, with ionic liquid molecules and/or atoms interspersed with polymer chain molecules and retained in the matrix by physical adsorption, molecular entanglements, or the ionic liquid can be retained in larger polymer segments and structures such as mesoporous polymer structures or microcellular polymer foam structures. Ionic liquids can be integrated with the polymer matrix using various known techniques, including but not limited to forming a solution that includes a polymer and an ionic liquid and casting a film from the solution, diffusing an ionic liquid into a pre-formed polymer membrane structure (e.g., by dipping or soaking), or melt-blending a polymer with an ionic liquid and casting or extruding a film from the blended melt or other polymer membrane forming techniques known in the art.

Ionic liquid cations or anions can also be grafted onto the membrane polymer so as to chemically retain ionic liquid in the polymer membrane. In one exemplary embodiment, an imidazolium is attached as a pendant group on a polymer backbone. For example, an imidazolium can be covalently tethered as a pendant group on a polymer's backbone (such as polyethylene, ref: U.S. Pat. No. 7,897,661) or a polymer's side chain (such as on the phenyl ring of polystyrene, ref: Langmuir 2004, 20, 596-605). In another exemplary embodiment, an imidazolium is incorporated into a polymer backbone. For example, an imidazolium can be inserted into a polyethylene backbone (ref: *Anal. Methods,* 2010, 2, 455-457) or a polyoxyalkylene ester backbone (ref: *Journal of Membrane Science,* 2011, 1-2, 1-4) to form main-chain imidazolium polymers. An anionic group (such as its corresponding H+ form acid, $X^\ominus$—$H^\oplus$), which can associate with imidazolium, can be directly added into imidazolium-containing polymer, or tethered on the same or different polymers and then mix, either intramolecular (the former cases) or intermolecular (the latter cases), with imidazolium to form an ionic-liquid cation/anion pair, see *Nature Materials,* 2009, 8, 621.

The amount of ionic liquid in the polymer membrane can vary depending on the parameters and desired performance of the MEA. For an ion conducting polymer such as Nafion, where ionic conductivity is dependent primarily on the side chain function groups, i.e, sulfonic groups ($SO_3^-$), its conductivity is determined by the density of those functional groups represented by equivalent weight (EW) (mass of dry Nafion per mole of sulfonic acid groups) and water content $\lambda$ given as $\lambda=(W_{H2O}$(g water/gram Nafion)$\times EW/M_{H2O})$. As an example, when water molecules are replaced by ionic liquids, the amount of ionic liquids can be represented by $\lambda$ as well, i.e., $\lambda=(W_{IL}$(g IL/gram Nafion)$\times EW/M_{IL})$. In an exemplary embodiment, the $\lambda$ of membrane with ionic liquids ranges from 0.1 to 5. The thickness of the membrane can also vary depending on the parameters and desired performance of the MEA. In an exemplary embodiment, the membrane has a thickness ranging from 1 micron to 500 micron, more specifically from 5 micron to 100 micron.

Exemplary polymers for the polymer membrane described herein can include any polymer capable of forming a matrix structure that is able to retain the ionic liquid. For larger matrix structures like mesoporous or microcellular structures, the polymer should form a structure having surface characteristics as well as porosity or cellular characteristics that allow the structure to retain the ionic liquid, and virtually any polymer capable of forming such structures may be used, including but not limited to polyesters (including polyoxyalkylene esters), polyolefins, polyurethanes, acrylic polymers, polyimide, polysulfone, polyarylsulfone, polybenzimidazole ("PBI"), co-polymers (e.g., poly-arylene-ether-sulfone co-polymers or block-copolymers), polyetherimide-siloxane copolymers, perfluorinated polymers (e.g., polytetrafluoroethylene ("PTFE"), and perfluoroalkoxy copolymer ("PFA")), and partially fluorinated polymers (e.g., polyvinylidene fluoride ("PVDF")). The type of polymer molecular structure can be important in selection of a polymer to retain an ionic liquid in a nano-scale polymer matrix. The polymer may be non-ionic or it may be ionic (e.g., DuPont Nafion® ionomer). Useful non-ionic polymers for retaining the ionic liquid on such a scale include but are not limited to polyoxyalkylene (i.e. polyoxyethylene), per- or partially fluorinated polymers (i.e. PFA, PTFE, PVDF), polystyrene, heteroaromatic polymers (such as polyaniline, polypyrrole, PBI). Useful ionic polymers may include ionic groups attached to a polymer so that the polymer has the ionic-exchange ability, such groups including but not limited to sulfonic acid, phosphonic acid, and sulfonimide acid. Exemplary ionomers include per-fluorinated sulfonic acid ("PFSA"), such as Nafion® ionomer and Solvey Solexis Auqivion™ ionomer, sulfonated polystyrene, sulfonated polysulfon, disulfonated poly(arylene ether sulfone) block-copolymers ("BPSH"). Conventional additives, e.g., surfactants, solvents (e.g., polyethylene glycol), and fine particles (such as functionalized of non-functionalized silica, carbon-based powders, metal-oxides particles) may also be added to the polymer matrix.

The electrode assemblies described herein are useful in gas sensors, the configurations of which can vary widely, and are well-known in the art. The MEA can function in environments of low or no humidity, and therefore the provision of a source of water vapor to the polymer membrane is optional, and in some embodiments the sensor is free of any water reservoir. In some embodiments, a water reservoir or other source of water vapor to the membrane may be useful. For example, humidity can impact the sensitivity of sensors utilizing exemplary embodiments of the electrode assemblies described herein, and providing a source of water vapor can provide a desired sensitivity.

In some embodiments, the sensor is a hydrogen sulfide sensor where the polymer membrane with ionic liquid functions as a proton exchange membrane, as described hereinabove. Such sensors can be operated by exposing the sensing electrode to the gas being sensed to generate a difference in electronegative potential between the sensing electrode and the reference electrode that is responsive to the presence and/or concentration of a component in a gas being tested, measuring voltage or current in an electrical circuit connecting the sensing electrode and the counter electrode, and converting the measured voltage or current to a reading indicative of the presence and/or concentration of the component in the gas being tested. Some exemplary embodiments of the sensors described herein (e.g., exemplary embodiments utilizing an acid salt anionic group-containing ionomer) may exhibit variations in sensitivity base on the humidity of the environment. Accordingly, in some exemplary embodiments, an algorithm for converting the measured voltage or current from the MEA can include functionality for adjusting the conversion based on the humidity of the environment, which can be determined based on the impedance or conductivity of the membrane using DC or AC impedance techniques. The impedance can be measured by applying an AC excitation with or without a DC bias at one or more frequencies (10-10000 Hz for example). This period is much shorter than CO detection time and the impedance measurement can be carried out while CO is being detected or when no CO is measured.

Figure 4:
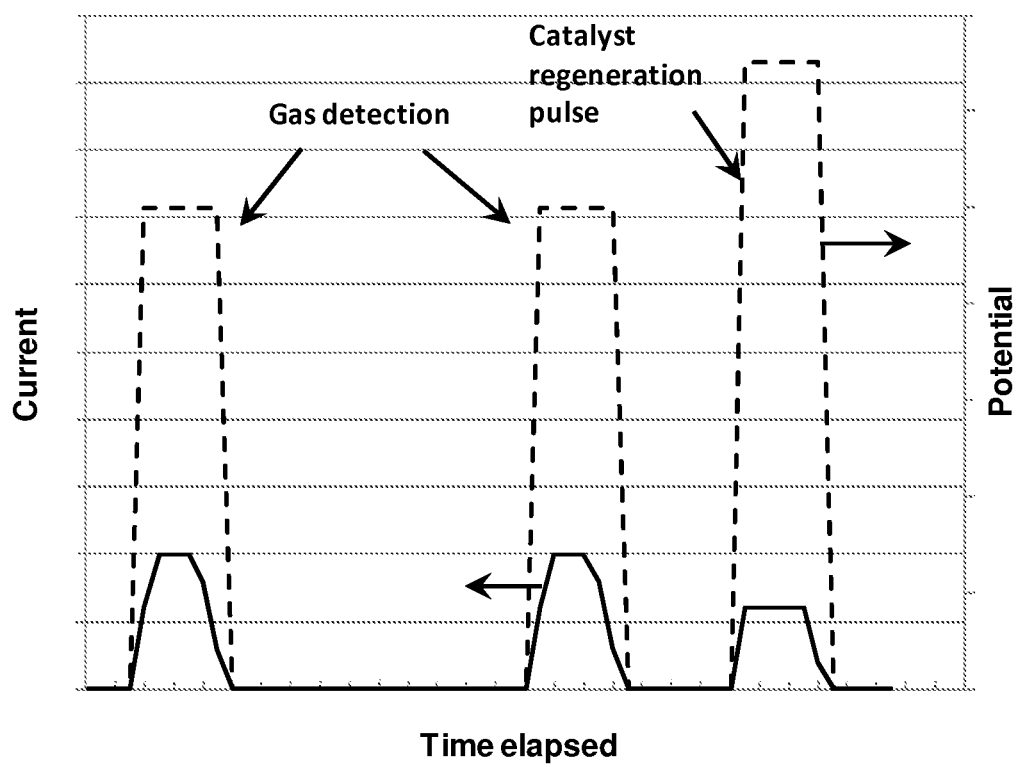
FIG. 4 depicts a voltage protocol for measurement of $H_2S$ concentration and also catalyst regeneration.

A gas sensor as described herein such as an $H_2S$ sensor has two primary operating modes, i.e. detection mode and regenerative mode. To remove contaminants on the catalyst surface, including elemental sulfur and other sulfur species, the sensing electrode is polarized according to a pre-set protocol to oxidize the contaminates and eject the resulting products to gas phase or an adsorbent disposed in close proximity of the sensing electrode. In an exemplary embodiment, positive potential pulses of varying duration are applied at a pre-set frequency in between gas sensing measurements with relaxation periods allowed to the sensor to restore baseline response. One exemplary voltage protocol is shown in FIG. 4 where one catalyst regeneration pulse is applied following detection of $H_2S$ by the sensor. As shown in the elapsed time plot of current (solid line) and voltage (dashed line) shown in FIG. 4, the first two peaks in current and voltage represent detection of $H_2S$, which cause the sensor circuitry (e.g., a microprocessor) to generate a catalyst regeneration pulse. The catalyst regeneration pulse(s)s can be applied along with other diagnostic and supervision pulses to ensure the functionalities of a sensor. Frequency and duration of regeneration pulses can vary in a wide range such as 0.1-10 Hz and 0.5-60 seconds/pulse.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A gas sensor comprising:
   a housing;
   a membrane electrode assembly disposed in the housing, the membrane electrode assembly comprising a sensing electrode comprising a catalyst on a conductive support, a counter electrode comprising a catalyst on a conductive support, and a polymer membrane disposed between the sensing electrode and the counter electrode, wherein said polymer membrane includes an ionic liquid retained therein;
   said housing including a reference gas chamber to which the counter electrode is exposed, and a test gas chamber to which the sensing electrode is disposed;
   a pathway for test gas to enter the test gas chamber;
   a measurement electrical circuit connecting the sensing electrode and the counter electrode;
   an electrical circuit configured to polarize the sensing electrode with positive voltage greater than 1.2 V versus Standard Hydrogen Electrode to remove contaminants from the catalyst when it is partially or completely deactivated by contaminants.

2. The sensor of claim 1, wherein said contaminants comprise sulfur.

3. The sensor of claim 1, wherein the catalyst conductive supports comprises a conductive doped or undoped metal oxide.

4. The sensor of claim 1, wherein the positive voltage applied to the sensing electrode is different than a gas detection voltage.

5. The gas sensor of claim 1, wherein the catalyst in the sensing electrode and/or the counter electrode is a catalytic metal or alloy comprising iridium, rhenium, palladium, platinum, copper, indium, rubidium, silver, or gold.

6. The gas sensor of claim 1, the sensor being free of a liquid water reservoir.

7. The sensor of claim 1, wherein the polymer membrane comprises a proton-conducting ionomer matrix.

8. The sensor of claim 7, wherein the ionomer has a molecular structure that comprises a hydrophobic portion and a hydrophilic portion, wherein the hydrophobic portion comprises a fluoropolymer repeat unit.

9. The sensor of claim 7, wherein the ionomer has a molecular structure that comprises a hydrophobic portion and a hydrophilic portion, wherein the hydrophilic portion comprises a sulfonic acid group, a phosphonic acid group, or a sulfonamide acid group.

10. The sensor of claim 1, wherein the ionic liquid is a proton-conducting ionic liquid.

11. The sensor of claim 1, wherein the ionic liquid comprises an imidazolium, pyridinium, tetralkylammonium, pyrrolidinium, trialkylsulfonium, pyrazolium, triazolium, thiazolium, oxazolium, pyridazinium, pyrimidinium, or pyrazinium cation.

12. The sensor of claim 1, wherein the ionic liquid comprises one or more cations according to the formula:

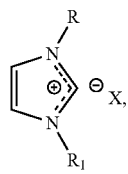

wherein R and R1 are independently H, substituted or unsubstituted alkyl of 1 to 30 carbon atoms, or substituted or unsubstituted aryl of 6 to 30 carbon atoms; and X is an anion.

13. The sensor of claim 12, wherein the ionic liquid comprises one or more anions selected from the group consisting of Cl, Br, $BF_4$, $PF_6$, $AlCl_4$, SCN, $HSO_4$, $HCO_3$, $CH_3SO_3$, $CH_3CH_2SO_4$, $(CH_3(CH_2)_3O)_2POO$, $(CF_3SO_2)_2N$, dicyanamide, $CF_3SO_3$, $(CF_3CF_2SO_2)_2N$, L-(+)-lactate, $CH_3SO_4$, and $CH_3COO$.

14. The sensor of claim 1, wherein either or both of the sensing electrode and the counter electrode has an ionic liquid retained within the electrode.

15. A method of sensing a gas, comprising:
   generating a difference in electrochemical potential between a sensing electrode comprising a catalyst on a conductive support and a counter electrode comprising a catalyst on a conductive support, the sensing electrode and the counter electrode separated by a polymer membrane that includes an ionic liquid retained therein, wherein said difference in electrochemical potential is responsive to the presence and/or concentration of a component in a gas being tested;
   measuring voltage or current in an electrical circuit connecting the sensing electrode and the reference electrode, converting the measured voltage or current to a reading indicative of the presence and/or concentration of the component in the gas being tested; and
   periodically applying an electrical potential difference across the sensing electrode and the counter electrode to polarize the sensing electrode with positive voltage greater than 1.2 V and remove contaminants from the catalyst when it is partially or completely deactivated by contaminants.

16. The method of claim 15, wherein said component is hydrogen sulfide and said contaminants comprise sulfur.

17. The method of claim 15, wherein either or both of the sensing electrode and the counter electrode further comprises a proton-conducting ionomer in which anionic liquid is retained.

18. The method of claim 15, wherein the conductive support comprises conductive metal oxides and the sensor is free of a liquid water reservoir.

19. The sensor of claim 1, wherein either or both of the sensing electrode and the counter electrode further comprises a proton-conducting ionomer.

20. The sensor of claim 14, wherein either or both of the sensing electrode and the counter electrode further comprises a proton-conducting ionomer in which the ionic liquid is retained.

21. The sensor of claim 20, wherein either or both of the sensing electrode and the counter electrode comprises an agglomerate comprising metal or metal oxide particles, catalyst particles, and the proton-conducting ionomer as a binder.

22. The sensor of claim 1, wherein the electrical circuit is configured to apply positive potential electrical pulses to the sensing electrode at a pre-set frequency in between gas sensing measurements, with relaxation periods allowed to the sensor to restore baseline response and/or by applying an electrical pulse following detection of $H_2S$ by the sensor.

* * * * *